United States Patent [19]
Keselman et al.

[11] Patent Number: 5,582,379
[45] Date of Patent: Dec. 10, 1996

[54] ADJUSTABLE LIMB SUPPORT SYSTEM

[75] Inventors: Yury Keselman, Beachwood, Ohio; George E. Skinner, San Rafel, Calif.; Richard R. Navarro, Strongsville, Ohio

[73] Assignee: Allen Medical Systems, Bedford Heights, Ohio

[21] Appl. No.: 412,148

[22] Filed: Mar. 28, 1995

Related U.S. Application Data

[63] Continuation-in-part of Ser. No. 265,647, Jun. 24, 1994.
[51] Int. Cl.⁶ .................................................. E04G 3/00
[52] U.S. Cl. ........................ 248/279.1; 5/621; 5/650; 248/229.25; 279/78; 403/105; 403/399
[58] Field of Search ............................ 248/273, 229.15, 248/229.25, 228.6, 230.6, 231.71, 291.1, 279.1; 403/105, 399, DIG. 9; 5/621, 624, 658, 648, 650, 651; 269/78

[56] References Cited

U.S. PATENT DOCUMENTS

| | | |
|---|---|---|
| 612,373 | 10/1898 | Allison . |
| 891,678 | 6/1908 | Downey . |
| 891,679 | 6/1908 | Downey . |
| 1,823,248 | 9/1931 | Allison . |
| 2,465,781 | 3/1949 | Banta . |
| 2,679,445 | 5/1954 | Roehm . |
| 4,526,355 | 7/1985 | Moore et al. ......................... 5/624 |
| 4,564,164 | 1/1986 | Allen et al. . |
| 4,615,516 | 10/1986 | Stullberg et al. . |
| 4,913,413 | 4/1990 | Raab . |
| 5,116,008 | 5/1992 | Allen ........................... 248/286.1 |
| 5,135,210 | 8/1992 | Michelson ........................... 5/658 |
| 5,157,800 | 10/1992 | Borders . |

Primary Examiner—Ramon O. Ramirez
Attorney, Agent, or Firm—Pearne, Gordon, McCoy & Granger

[57] ABSTRACT

An adjustable limb support system is provided for an operating room table to adjustably orient and position a stirrup or boot. The support system provides an adjustable support in combination with a vertically adjustable support. The vertically adjustable support includes a support arm, a ratchet wheel, a lock pin, and a ratchet release. The support arm is connected to a housing which both rotate about the ratchet wheel in a rotational plane extending upwardly and outwardly from the operating room table for automatic abduction. The lock pin engages the ratchet wheel and allows the support arm to be rotated upwardly but not downwardly. The ratchet release disengages the lock pin and allows the support to be rotated downwardly. The support arm can thus ratchet upwardly to fixed vertical positions and be lowered only by disengaging the lock pin. The adjustable support includes a retaining block, a compression block, and a compression head. The retaining block defines a passage for receiving a connecting rod secured to the stirrup or boot. The compression block defines a passage for receiving the support arm of the vertical adjustable support. The compression head when tightened prevents translation and rotation of the compression block on the support arm, and rotation of the compression block and the retaining block relative to each other. When the compression head is untightened the compression block can be translated or rotated on the support arm, and the blocks can be rotated relative to each other, in order to orient and position the stirrup or boot. The stirrup or boot freely rotates or swings about the axis of the connecting rod at all times.

20 Claims, 7 Drawing Sheets

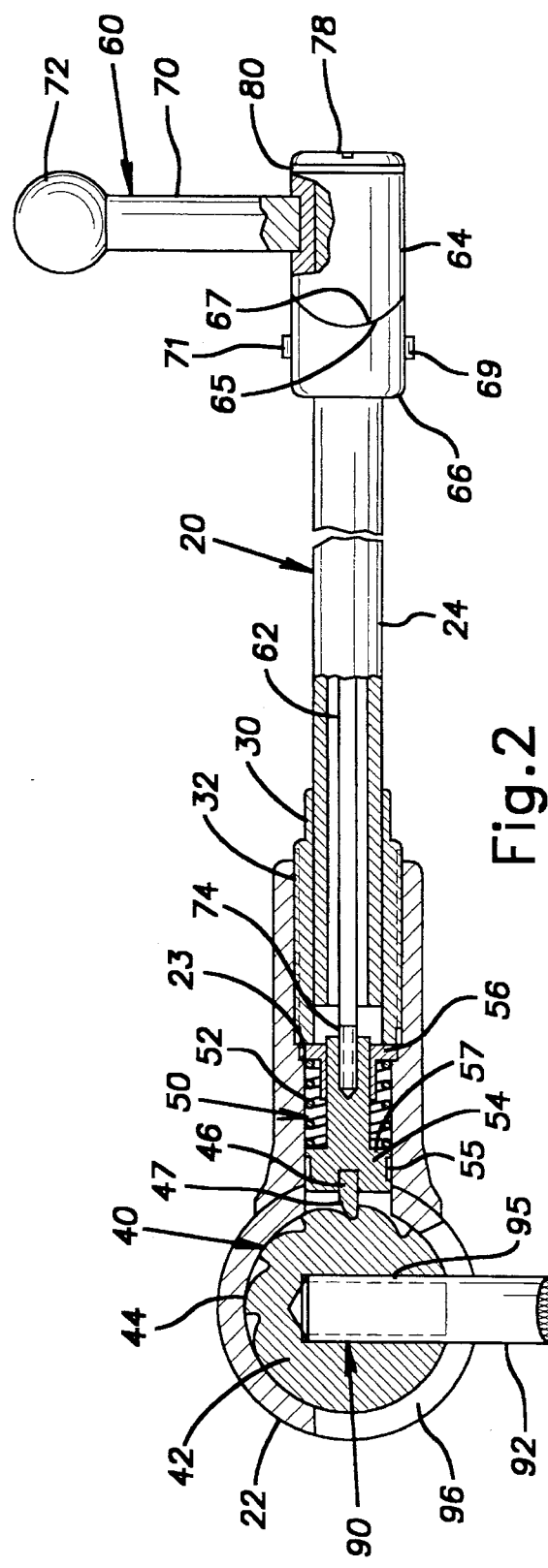
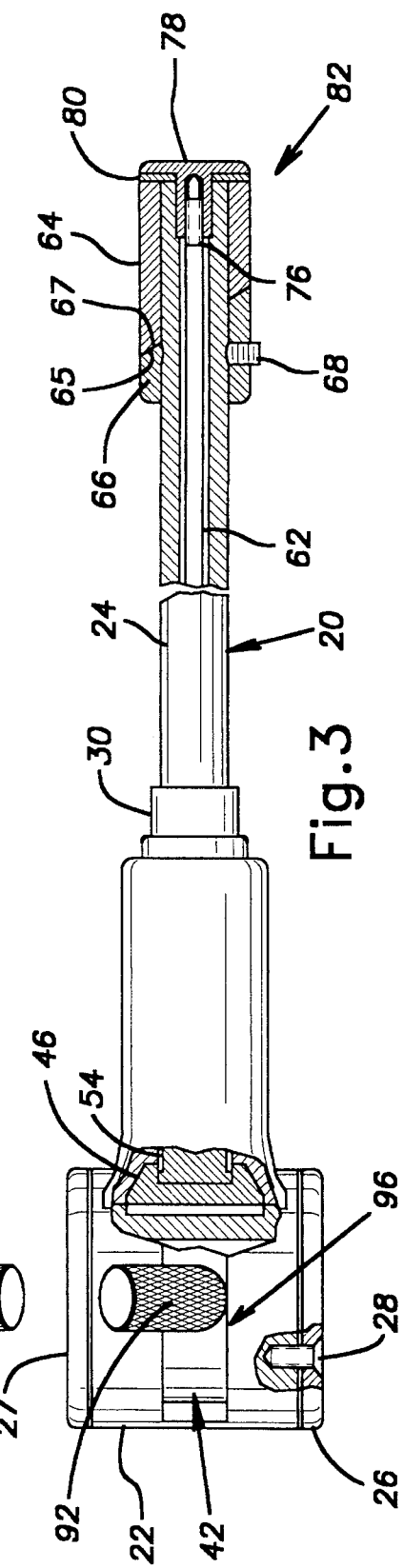

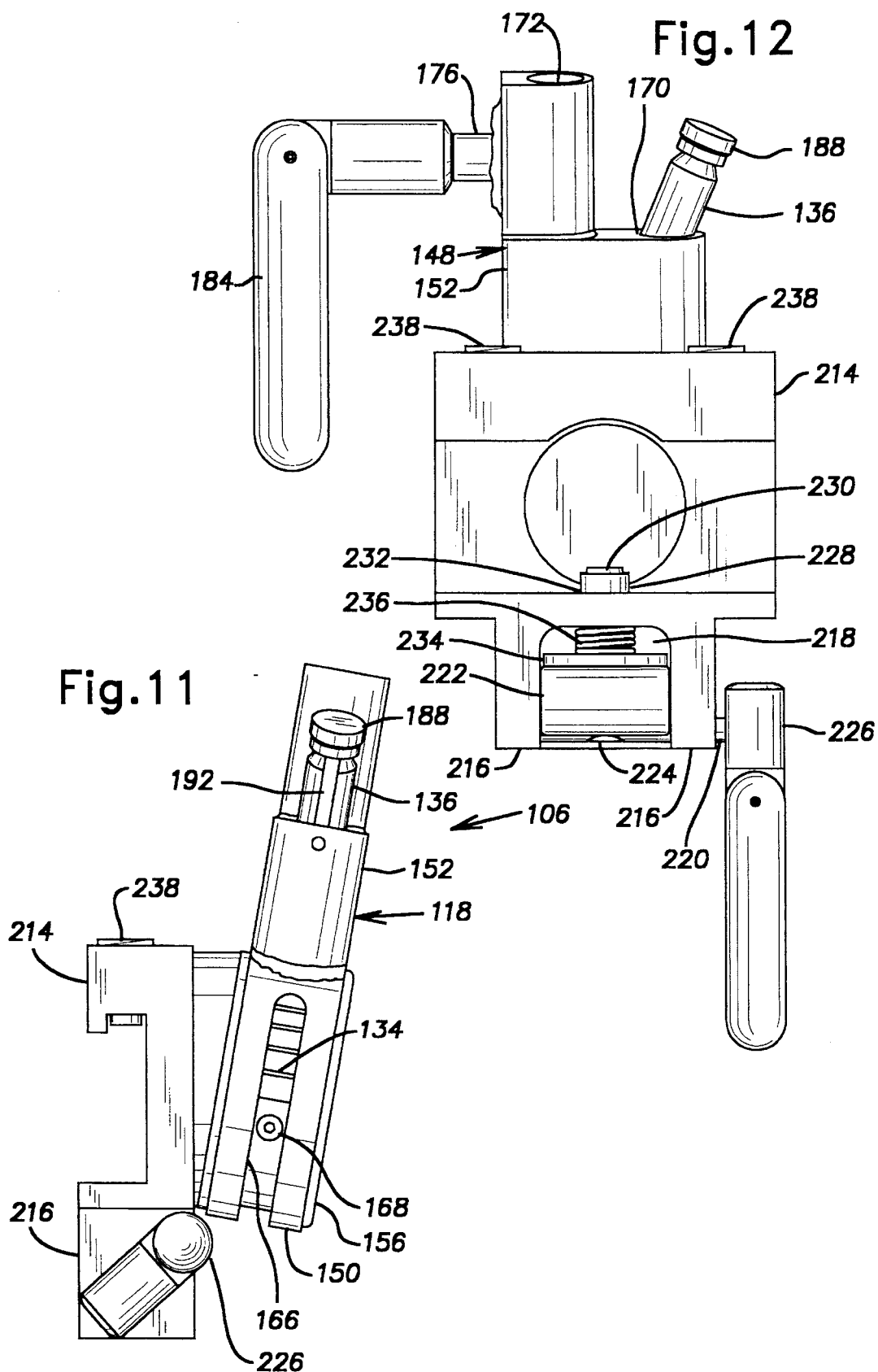

ADJUSTABLE LIMB SUPPORT SYSTEM

This is a continuation-in-part of application Ser. No. 08/265,647, filed Jun. 24, 1994.

BACKGROUND OF THE INVENTION

The present invention generally relates to an adjustable support system for holding in place the limb of a person during surgery, and more specifically, to such a system having an adjustable support in combination with a vertically adjustable support.

Adjustable support systems are known in the prior art. For example, U.S. Pat. No. 4,564,164 describes an adjustable support system having rotational and translational freedom. The system can be adjusted to a desired position and locked in place by one handle. In a limb support application, a limb support is attached to the adjustable support system with a bracket and the adjustable support system is attached to an operating room table with a rod. The rod is positioned horizontally, and has a right angle bend to a vertical portion which is clamped in a socket located on a side of the operating room table. The height and rotational position of the limb support are adjusted by moving and rotating the vertical portion of the rod within the socket. While the support system has rotational and translational freedom adjustable by one handle, the system has minimal height adjustment. The minimal height adjustment severely limits the number of positions that can be obtained to expose the patient. The vertical height of the system also cannot be readily adjusted during surgery and requires a minimum of two people to make the adjustment. Additionally, because the rod remains in a horizontal position, the rod may impair the access of assistants standing beside the doctor.

Limb supports incorporating various ratchet mechanisms for adjusting their vertical position are also known in the prior art. For example, U.S. Pat. No. 2,679,445 discloses a support for a stirrup on a physician's examining table. The stirrup bar ratchets upward to position the stirrup at a desired height. While the stirrup support does have a vertical height adjustment, the stirrup can only be adjusted and locked in position lengthwise along the stirrup bar. Additionally, the stirrup can only be rotated about one axis and the position cannot be locked in place. The limb support system, therefore, has a limited number of positions that can be obtained to expose a patient during a procedure. See also U.S. Pat. Nos. 1,823,248, 891,679, and 891,678 for related limb support systems wherein a ratchet mechanism adjusts the vertical height of a limb support.

U.S. Pat. No. 5,157,800 discloses a foot section for a birthing bed. A plate ratchets upward about its base to adjust the vertical position of a calf support. The calf support is mounted to the plate by means of a ball joint. The ball joint allows the angular position of the calf support to be adjusted and locked in place. While the calf support does have a vertical height adjustment and rotational freedom that can be locked, it does not have the freedom to translate along or away from the plate. The system, therefore, has a limited number of positions that can be obtained to expose a patient during a procedure. Moreover, the calf support's lack of translational freedom away from the vertical support may impair the access of assistants standing beside the doctor.

U.S. Pat. No. 612,373 discloses a physicians table. An arm ratchets upward about its base to adjust the vertical position of a stirrup. The stirrup position can be adjusted by translation lengthwise along the arm and radially away from the axis of the arm. Each adjustment, however, is locked in position by separate thumb-screws. Additionally, the stirrup can only be rotated about one axis and the position cannot be locked in place. The limb support system, therefore, has a limited number of positions that can be obtained to expose a patient during a procedure. Moreover, the available adjustments cannot be readily made during a procedure.

Each of the aforementioned patents are incorporated herein in their entirety by reference.

In general the prior art limb support means are able to hold a limb during surgery. However, some prior art limb supports lack a vertical adjustable support. Other prior art limb supports do not have both rotational and translational freedom. Yet other prior art limb supports do not lock the limb support position, do not lock the limb support position with one device, or fully lock all freedom of the limb support. In each case, the results are unsatisfactory. Therefore, there is a need in the art for an improved limb support system.

SUMMARY OF THE INVENTION

The present invention provides an adjustable limb support system by combining an adjustable support that orients and positions a stirrup or boot that supports a person's limb, and a vertically adjustable support which readily ratchets to adjust the height of the adjustable support and the stirrup or boot. The vertically adjustable support rotates in a plane of rotation extending angularly outwardly from the side of the table. The adjustable support is adapted for rotation of the stirrup or boot about an axis generally perpendicular to a plane of rotation of the vertically adjustable support, and two axes at right angles to the first axis. In a locked state the adjustable support locks the orientation of the stirrup or boot about the two axes, but the stirrup or boot floats or freely swings about the axis generally perpendicular to the plane of rotation of the vertically adjustable support. The result achieved by the combination of the adjustable support and the vertical adjustable support, is a support system that holds the patient's limb in positions which expose areas of the patient for surgery in ways never before obtainable. In addition, the combination gives one person the ability to make quick adjustments to the patient's position during a procedure and provides an access area for technicians to work along the side of the doctor.

In the present invention, the vertically adjustable support is provided to position the stirrup or boot and the adjustable support to various heights and different abduction angles. The vertically adjustable support comprises a support arm, a ratchet mechanism, a ratchet release, and an attachment. The adjustable support is secured to the support arm and is supported thereby. The ratchet mechanism allows the support arm to be readily rotated to fixed positions by simply applying a force to the support arm. The ratchet mechanism will not allow the support arm to be rotated back, therefore, a ratchet release is provided. The attachment enables the vertically adjustable support to be secured to an operating room table.

The adjustable support is provided to orient or position the stirrup or boot at each height or fixed vertical position and partially lock it in place. In an unlocked state the adjustable support, and the attached stirrup or boot, can be rotated about the support arm of the vertically adjustable support. Additionally, the stirrup or boot can be rotated about a second axis generally perpendicular to the support arm of the vertically adjustable support. In a locked state the adjustable support is locked to prevent the above stated rotations. The stirrup or boot can generally rotate or swing at all times about a third axis which is at right angles to the first and second axes.

It is a principle feature of the present invention that it provides a support system wherein the position and orientation of the stirrup or boot is adjustable at each of several heights or vertical positions. It is another feature of the present invention that it provides a support system that positions the patient during surgery to provide exposures of the patient that could not previously be obtained. It is a further feature of the present invention that it provides a support system that can be easily adjusted or positioned quickly and by one person.

It is an important feature of the present invention that it provides a combination of the adjustable support and the vertically adjustable support to allow the doctor to readily position or reposition the boot during a procedure as it becomes necessary. It is another important feature of the present invention that it provides a vertically adjustable support that can be vertically adjusted to positions other than horizontal so that assistants can stand and work beside the doctor without reaching over a horizontally positioned and when adjusted provides automatic exposure for technicians to work. It is a further important feature of the present invention that the stirrup or boot floats or freely rotates about the axis generally perpendicular to the rotational plane of the vertically adjustable support so that the boot automatically adjusts when the height or vertical position is changed. It is yet a further feature of the present invention that it provides an angled or bent attachment in order that the vertically adjustable support extends angularly outwardly from the operating room table to obtain automatic abduction of the patient. It is also a further feature of the present invention that it provides a vertical adjustable support having a maximum angular position that reduces patient risk due to excess hip flexion.

The foregoing and other objectives, features, and advantages of the present invention will be more readily understood upon consideration of the following detailed description of the invention in conjunction with the accompanying drawings.

BRIEF DESCRIPTION OF THE DRAWINGS

The present invention will hereafter be described with reference to the drawing figures, wherein:

FIG. 2 is an elevational view, partially in cross section, of the vertically adjustable support of FIG. 1 with the lock pin in a locked position;

FIG. 3 is a plan view, partially in cross section, of the vertically adjustable support of FIG. 2;

FIG. 11 is a side elevational view of a variation of the ratcheting table clamp of FIG. 7; and FIG. 12 is a rear elevational view of the ratcheting table clamp of FIG. 11.

DETAILED DESCRIPTION OF PREFERRED EMBODIMENTS

Figure 5:
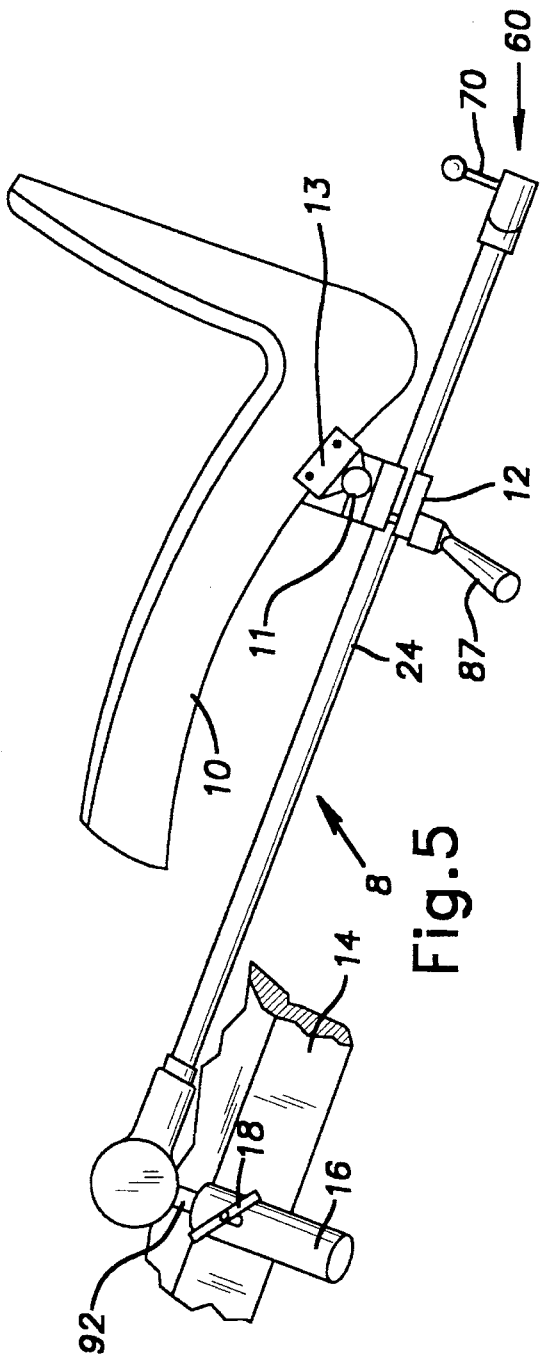
FIG. 5 is a perspective view of a first embodiment of a limb support system including the vertically adjustable support of FIG. 1.

An adjustable limb support system according to a first embodiment of the invention is shown in FIG. 5. The system comprises a vertically adjustable support 8, a floating or swinging boot 10, and an adjustable support 12.

Figure 1:
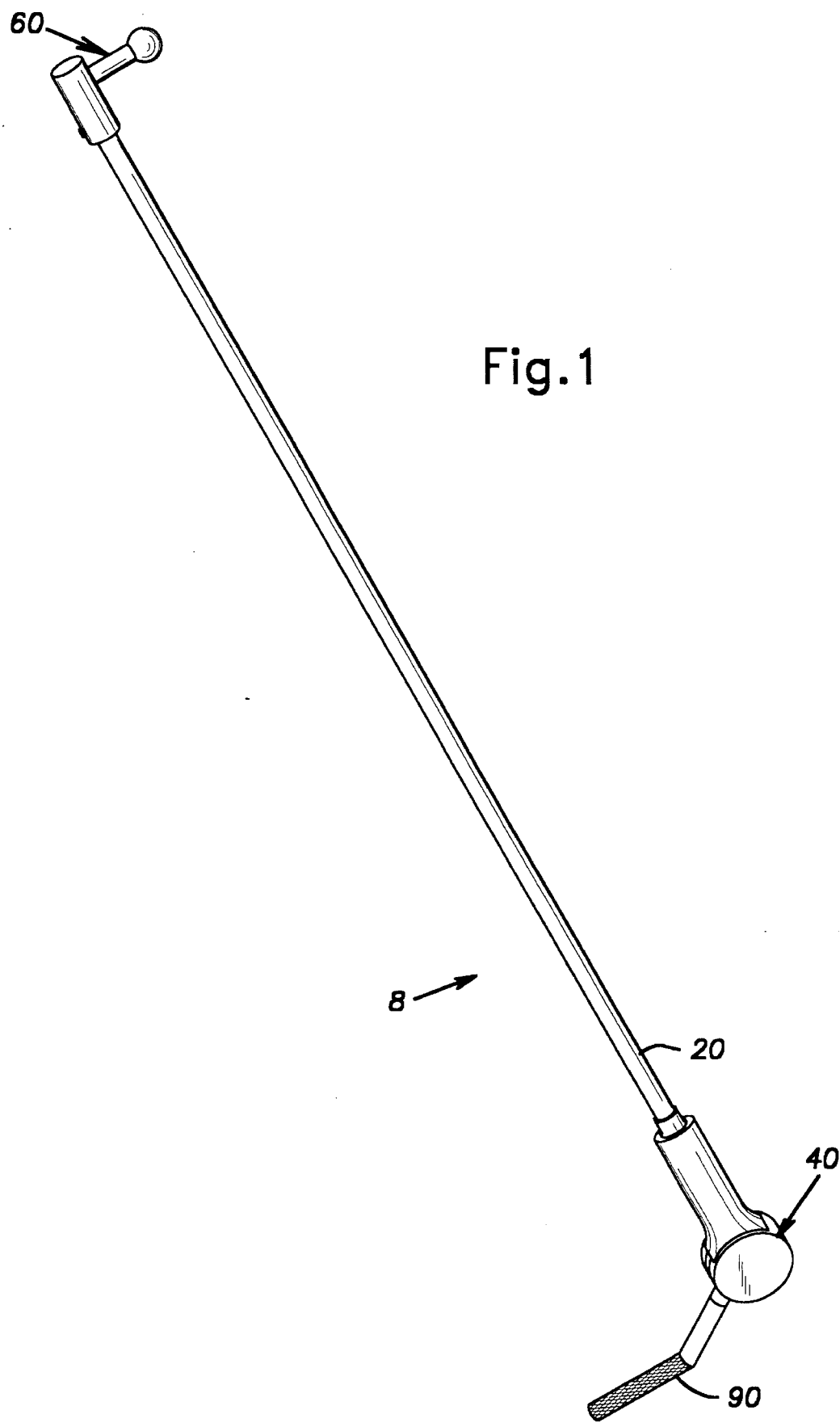
FIG. 1 is a perspective view of a vertically adjustable support.

The vertically adjustable support 8 is best shown in FIG. 1. At one end of the vertically adjustable support 8 is an attachment 90 which secures the vertically adjustable support 8 to an operating room table 14 (as shown in FIG. 5). The attachment 90 is fixed to a ratchet mechanism 40. The ratchet mechanism 40 allows a support arm 20 to rotate upwardly to fixed angular positions. At an end of the support arm 20 opposite the attachment 90 is a ratchet release 60 which allows the support arm 20 to rotate downwardly to fixed angular positions.

A detailed view of the preferred embodiment of the vertical adjustable support 8 is shown in FIGS. 2 and 3. The support arm 20 comprises a tube 24 and a housing 22. The housing 22 has two cylindrically shaped cavities perpendicular to each other. The first cavity is open at each end while the second cavity is open at one end and opens into the first cavity at the other end. The second cavity has a step 23 between two diameters, with the larger diameter towards the open end. The larger diameter of the second cavity is internally threaded 32. The two open ends of the housing's 22 first cavity are covered by end caps 26, 27 which are each attached to the housing 22 by two flat head screws 28.

The tube 24 is circular in cross-section and contained at one end within a tube housing 30. The tube housing 30 is tubularly shaped and has a threaded outer surface 32 which mates with the internal threads of the housing's 22 second cavity. The inner diameter of the tube housing 30 is sized to receive the outer diameter of the tube 24. The outer diameter of the tube 24 is sized to mate with the adjustable support 12 (as shown in FIG. 5).

It will be observed that other embodiments of the support arm 20 known to those skilled in the art are possible. For example, the tube 24 could have a forked-end which sits astride the ratchet wheel 42 and pivots about a pin in the center of the ratchet wheel 42.

The ratchet mechanism 40 consists of a ratchet wheel 42 and a lock pin 46 as seen in FIG. 2. The outer diameter of the ratchet wheel 42 is sized to fit within the first cavity of the housing 22 so that the housing 22 and the tube 24 can rotate around the ratchet wheel 42 about the centerline of the housing's 22 first cavity and ratchet wheel 42.

As seen in FIG. 2, the outer diameter of the ratchet wheel 42 has a plurality of serrations 44. Each serration 44 has a rounded upper edge and a radial lower edge. The lock pin 46 has a protruding end 47 shaped to engage the ratchet wheel 42 serrations 44 and lock the housing 22 and the tube 24 in position. The ratchet wheel 44 of the preferred embodiment has five serrations 44 which lock the tube 24 in five fixed angular positions. It will be observed that a greater or fewer number of fixed angular positions could be utilized. The fixed positions of the preferred embodiment are −26, 0 (horizontal), 26, 52 and 78 degrees. The zero degree, or horizontal, position is shown in FIGS. 2 and 3. In order to lock the tube 24 in a fixed position, the lock pin 46 is urged into the serration 44 by a spring element 50.

It will be observed that other fixed angular positions can be utilized, however, the preferred maximum angular position is 78 degrees in order to reduce patient risk. A 90 degree position would result in pressure in the trocar area. If the surgeon requires the patient's limb to be vertical or 90 degrees, it can be accomplished by adjusting the vertically adjustable support to the 78 degree position and gaining an additional 12 degrees by tilting the table 14. This eliminates the pressure on the trocar area and reduces patient risk of excess hip flexion.

As seen in FIG. 2, the preferred embodiment of the spring element 50 is a helical coil compression spring 52 with a lock body 54 and spring cap 56. The spring 52 must have a spring force large enough to hold the lock pin 46 in the serration 44 of the ratchet wheel 42 when a limb is being supported. The spring force must also be small enough so that it can be easily overcome by the ratchet release 60. In the preferred embodiment, the spring 52 is one inch long with a 0.845 inch outer diameter and made of 0.085 inch diameter music wire. It will be noted that other embodiments of the spring element 50 known to those skilled in the art are possible, such as a leaf spring.

The lock body 54 is cylindrically shaped having a step 57 between two diameters, as seen in FIG. 2. The larger diameter is sized to slide within the smaller diameter of the housing's 22 second cavity. Preferably the large diameter is recessed 55 to ease sliding within the housing 22. The smaller diameter is sized to fit within the inner diameter of the spring 52. The lock pin 46 is fixed to the large diameter end of the lock body 54. The spring cap 56 is tubularly shaped with an inner diameter sized to slide over the small diameter of the lock body 54, and an outer diameter sized to fit within the inner diameter of the spring 52. The spring cap 56 also has a flange with a diameter sized to fit within the large diameter of the housing's 22 second cavity.

As best seen in FIG. 2 the flange of the spring cap 56 is held against the step 23 in the housing's 22 second cavity by the tube housing 30. The spring is retained between the flange of the spring cap 56 and the step 57 on the lock body 54. Because the spring cap 56 is fixed to the housing 22, the spring 52 urges the lock body 54 towards the ratchet wheel 42 so that the lock pin 46 engages a serration 44 on the ratchet wheel 42 to lock the housing 22 and the tube 24 in position.

When a higher fixed position is desired, an upwardly directed force is applied to the tube 24. As the tube is pushed upward the housing 22 and tube 24 rotate about the centerline of the ratchet wheel 42. As the upward force is applied to the tube 24, the protruding end 47 of the lock pin 46 follows the rounded upper edge of the serration 44 slightly compressing the spring 52 until the next serration 44 is reached. Once the next serration 44 is reached, the spring 52 urges the lock pin 46 into the next serration 44 to lock the housing 22 and tube 24 in the new angular position. The procedure is repeated if yet a higher fixed position is desired.

Because of the serration 44 has a radially extending lower edge, the tube 24 cannot be lowered by merely applying a downward force on the tube 24. Therefore, a ratchet release 60 is provided to disengage the lock pin 46 from the serration 44. Once the lock pin 46 is disengaged the tube 24 can be lowered. The ratchet release 60 comprises a traction rod 62, a cam 64, and a cam base 66 as seen in FIGS. 2 and 3. The traction rod 62 is an elongated rod with a diameter sized to fit within the tube 24. A first end of the traction rod 62 is fixed to the lock body 54. In the preferred embodiment, the end of the traction rod 62 is threaded 74 and mates to an internally threaded hole formed in the small diameter end of the lock body 54 and is spot welded.

The cam 64 and the cam base 66 are tubularly shaped having an inner diameter sized to slide over the outer diameter of the tube 24. The upper surface 67 of the cam base 66 is angled in relation to its centerline. The lower surface 65 of the cam 64 is angled in relation to its centerline so that it will contact and mate with the upper surface 67 of the cam base 66. The cam base 66 forms three internally threaded holes located 90 degrees from each other and sized to cooperate with set screws 68, 69, 71. The set screws 68, 69, 71 prevent movement of the cam base 66 relative to the tube 24.

The cam 64 is connected 82 to a second end 76 of the traction rod 62. In the preferred embodiment the connection 82 is made by an end cap 78. The end cap 78 has a cylindrical portion with a diameter sized to fit within the inner diameter of the tube 24 and a flange portion with a diameter sized to retain the cam 64 on the tube 24. The cylindrical portion of the end cap 78 forms an internally threaded hole which mates with threads formed by the second end 76 of the traction rod 62. The cam base 66 position along the axis of the tube 24 is adjusted to ensure that the cam 64 is constrained between the cam base 66 and the end cap 78. Preferably a polytetrafluoroethylene, commercially sold as TEFLON, washer 80 is located between the cam 64 and end cap 78. The TEFLON washer 80 reduces the friction between the cam 64 and end cap 78 and thereby eases the rotation of the cam 64.

It will be observed that other embodiments of the connection 82 between the cam 64 and traction rod 62 known to those skilled in the art are possible. For example, the end cap 78 could be rigidly attached to the cam 66 with the traction rod 62 passing through the end cap 78 having a restraint attached to restrain the end cap 78 and cam 64.

Figure 4:
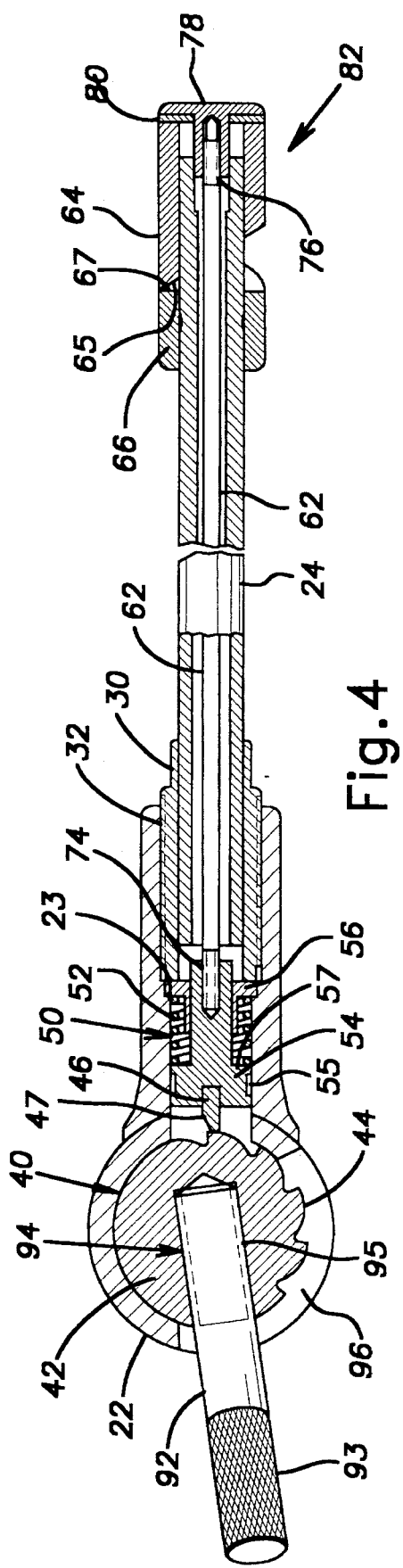
FIG. 4 is an elevational view, partially in cross section, of the vertically adjustable support of FIG. 2 with the lock pin in a released position.

The lock pin 46 disengaged from the ratchet wheel 42 is best shown in FIG. 4. As seen in FIGS. 2 and 4, to release the ratchet mechanism 40, a handle 70 provided with a grip 72 is turned to rotate the cam 64 about the tube 24. As the cam 64 rotates, the cam's angled contact surface 65 rides up the angled contact surface 67 of the cam base 66. As the cam 64 rides up the cam base 66, the end cap 78 is urged outward thus causing the traction rod 62 to pull the lock body 54 outward by compressing the spring 52 until the lock pin 46 disengages from the serration 44 on the ratchet wheel 42. Once the lock pin 46 is disengaged, the housing 22 and the tube 24 can be rotated downward about the ratchet wheel 42 to a new vertical position. The handle 70 is then turned in the opposite direction to return the cam 64 and traction rod 62 back to their original position causing the spring 52 to urge the lock pin 46 back into engagement with the ratchet wheel 42 serration 44 at the new vertical position.

As seen in FIG. 2, the attachment 90 consists of a post 92 having a bend and is secured to the ratchet wheel 42. The post 92 is preferably bent such that an end portion 93 angularly extends from the rotational plane about the ratchet wheel 42 when the post 92 is firmly attached to the ratchet wheel 42. The post 92 is bent preferably an angle in the range of 10 degrees to about 30 degrees, and more preferably, an angle of about 20 degrees. It will be noted that the post could be bent to other angles. The post 92 is bent so that the vertically adjustable support 8 extends outwardly from the side of the table 14 to which it is attached (FIG. 5). This positions the stirrup or boot 10 to automatically abduct or separate the limbs of the patient.

In the preferred embodiment, the post 92 is secured by a threaded and pinned end 95 which mates to an internally threaded hole formed in the ratchet wheel 42. It will be noted that the post 92 could be secured by other methods known to those skilled in the art. For example, the post 92 could be welded to the ratchet wheel 42. The post 92 extends from the ratchet wheel 42 through an opening 96 formed by the housing 22. The post 92 length is sized to locate the adjustable vertical support 8 at a range of desired heights. The post end portion 93 preferably is knurled to allow the post 92 to be more readily clamped to the operating room table 14 (as seen in FIGS. 2 and 5).

It will be observed that other embodiments of the attachment 90 known to those skilled in the art are possible. For example, the attachment 90 could consist of a bracket with two flanges that are rigidly fixed to opposing sides of a ratchet wheel that extends out of the two openings of the housing's 22 first cavity. The lower side of the bracket could have a pin that would allow rotation of the system and easily be clamped to the operating room table 14

In the preferred embodiment a thread locking compound is applied to the threaded connections between the tube housing 30 and the housing 22, the traction rod 62 and the end cap 78, and the post 92 and the ratchet wheel 42, as seen in FIG. 2. Other fastener locking devices known to those skilled in the art are possible and could be utilized to prevent the loosening of the threaded connections after repeated usage of the vertically adjustable support 8.

As shown in FIG. 5, the boot 10 is provided with a transversely extending connecting rod 11. Preferably the connecting rod 11 is welded, or otherwise connected, to a bracket 13 fastened to the boot 10. When the connecting rod 11 is retained within the adjustable support 12, the boot 10 can generally float or freely rotate about the axis of the connecting rod 11.

Figure 6:
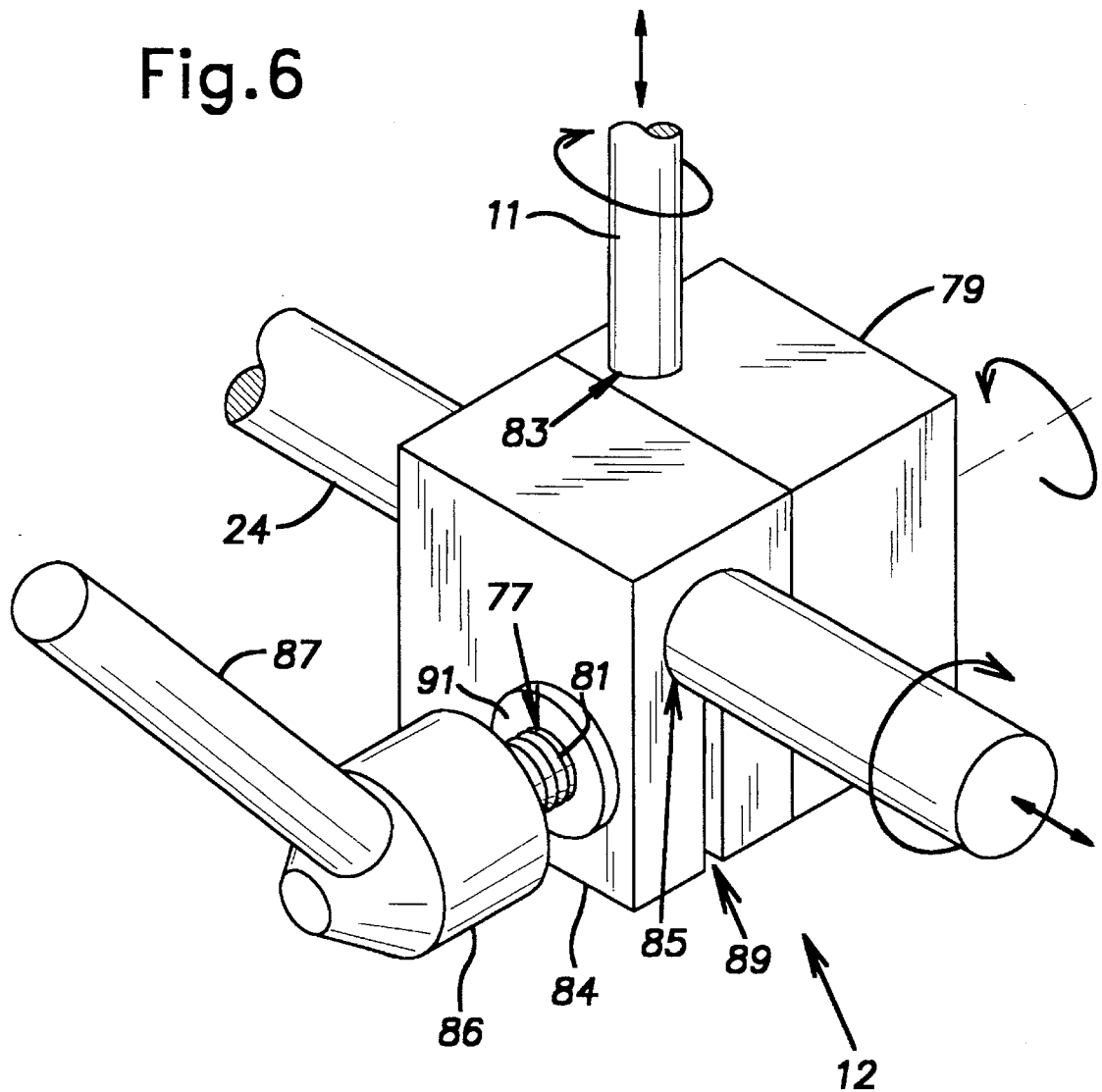
FIG. 6 is a perspective view of an adjustable support.

As seen in FIG. 6, the preferred embodiment of the adjustable support 12 comprises a retaining block 79, a compression block 84, a compression head 86, a washer 91, and two set screws (not shown). Each block defines a cylindrical passage 83, 85 for receiving the connecting rod 11 and tube 24 respectively. The cylindrical passage 83 in the retaining block 79 is sized to contain the connecting rod 11 secured to the limb support or boot 10 (as seen in FIG. 5). The cylindrical passage 85 in the compression block 84 is sized to receive the tube 24 of the vertical adjustable support 8 (as seen in FIG. 5). The compression block 84 defines a slot 89 which extends from one edge of the compression block 84 to the cylindrical passage 85. The blocks 79, 84 further define a hole 77 at right angles to the cylindrical passages 83, 85, and through the slot 89. The hole 77 is internally threaded at a portion within the retaining block 79. The retaining block 79 also defines two internally threaded holes or openings (not shown) extending from a back surface to the cylindrical passage 83 to cooperate with the set screws. One set screw contacts the boot connecting rod 11 to control the ease of rotation of the boot 10 about the axis of the connecting rod 11 and the other set screw controls the angle.

As seen in FIG. 6, the compression head 86 has a threaded member 81 and a handle 87. The threaded member 81 is inserted through the hole 77 and cooperates with the internal threads defined in the retaining block 79. The washer 91 is located on the threaded member 81 between the compression head 86 and the compression block 84 to decrease friction and provide smoother tightening of the compression head 86. Preferably the washer is made of nylon. When the compression head 86 is tightened, the slot 89 closes slightly to the lock orientation and position of the adjustable support 12 relative to the tube 24 of the vertical adjustable support 8. When the compression head 86 is not tightened, the adjustable support 12 can translate along the tube 24 of the vertical adjustable support 8 and can be rotated about the tube 24. Additionally the retaining block 79 and compression block 84 can be rotated relative to each other in the unlocked position.

Referring to FIG. 5, the invention is shown in a leg support application. The vertically adjustable support 8 is in the zero degree or horizontal position. The post 92 is removably secured in socket 16 and rotationally held by clamp 18. The socket 16 is typically a fitting located on the side of an operating room table 14. Due to the bend in the post 92, the vertically adjustable support 8 extends angularly outwardly from the side of the table 14. The adjustable support 12 is received on the tube 24 of the vertically adjustable support 8. The adjustable support receives the connecting rod 11 which is secured.

A second adjustable limb support system according to the invention is typically secured to the opposed side of the table 14 in the same manner by a post bent in the opposite direction (not shown). In this configuration a patient lies with their back on the table and a leg portion or foot in each boot.

As seen in FIG. 5, the orientation and position of the leg, can be adjusted by both the adjustable support 12 and the vertically adjustable support 8. The surgeon can unlock the adjustable support 12 by turning the handle 87. The adjustable support 12 can then be translated along or rotated about the axis of the tube 24. The retaining block 79 and attached boot 10, can also be rotated relative to the compression block 84 about an axis perpendicular to both the axis of the connecting rod 11 and the axis of the tube 24. Additionally, or alternately, the surgeon can raise the adjustable support 12 to any of the fixed positions or vertical heights by pushing upwardly on the tube 24. The vertically adjustable support 8 automatically locks into one of the fixed positions or vertical heights. When the desired orientation and position of the limb support 10 are obtained, the adjustable support system 12 is locked by turning the handle 87 back to the tightened position. It should be noted that the boot 10 floats or is free to swing or rotate about the axis of the connecting rod at all times. Therefore, the vertically adjustable support 8 can be raised or lowered in many situations without unlocking the adjustable support 12 because the floating or swinging boot 10 will automatically adjust for the new position.

If necessary, the surgeon can lower the vertically adjustable support 8 to one of the fixed positions or vertical heights by turning the handle 70. When a desired position is obtained the handle 70 is returned to its original position and the tube 24 is locked in place. The above described adjustments can be made in any combination and whenever the surgeon desires the limb to be in a new orientation or position. As can be seen by the above described adjustments, they can be readily made by one person during surgery.

Figure 10:
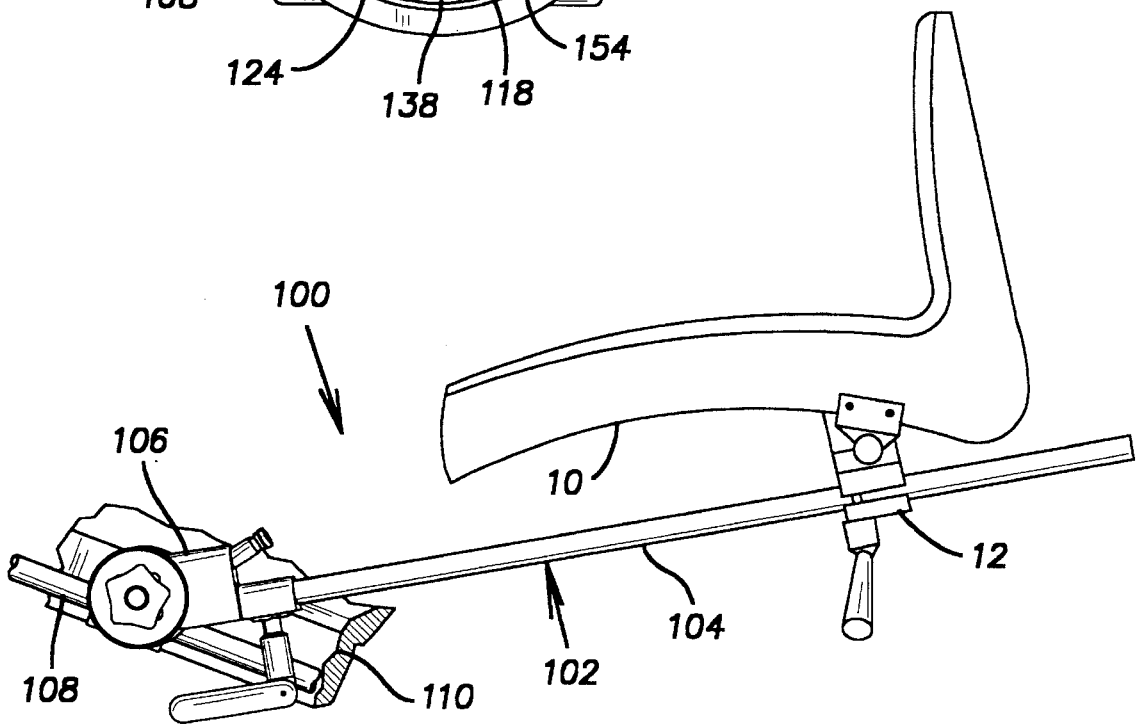
FIG. 10 is a perspective view of a second embodiment of a limb support system including the ratcheting table clamp of FIG. 7.

An adjustable limb support system 100 according to a second embodiment of the invention is shown in FIG. 10. The system 100 includes a vertically adjustable support 102, an adjustable support 12 and a boot 10. The adjustable support 12 and the boot 10 are the same as described above in the description of the first embodiment. The vertically adjustable support 102 includes a support arm 104, such as a tube or rod, and a ratcheting table clamp 106. The table clamp 106 secures the vertically adjustable support 102 to a side rail 108 of operating room table 110.

Figure 7:
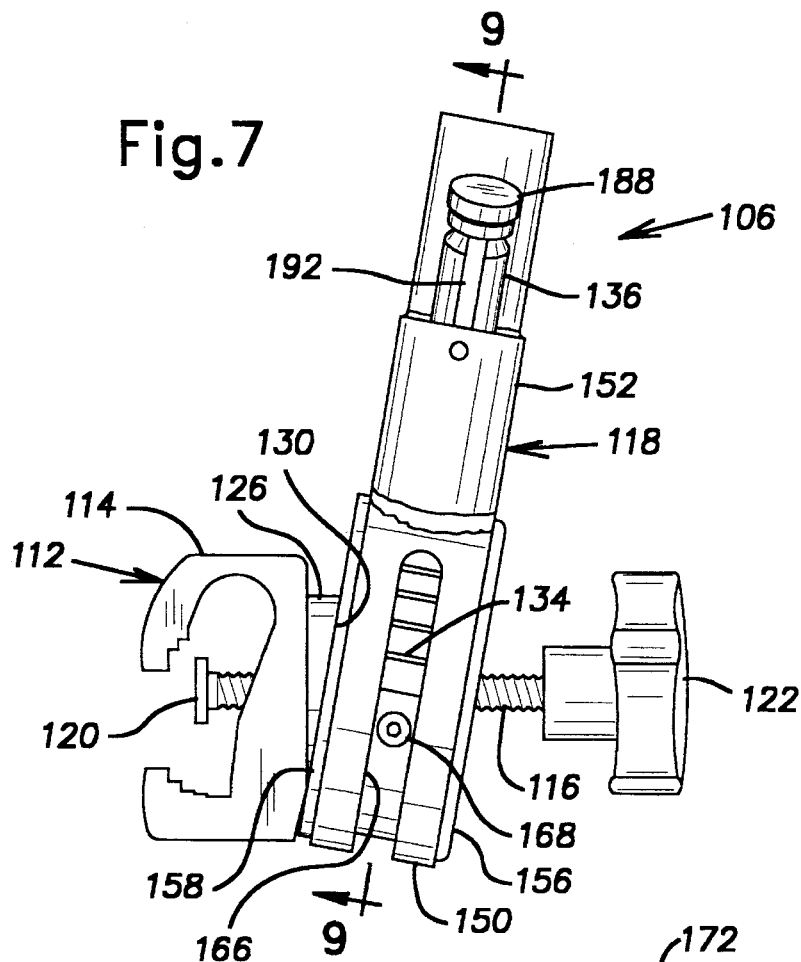
FIG. 7 is a side elevational view of a ratcheting table clamp.
Figure 8:
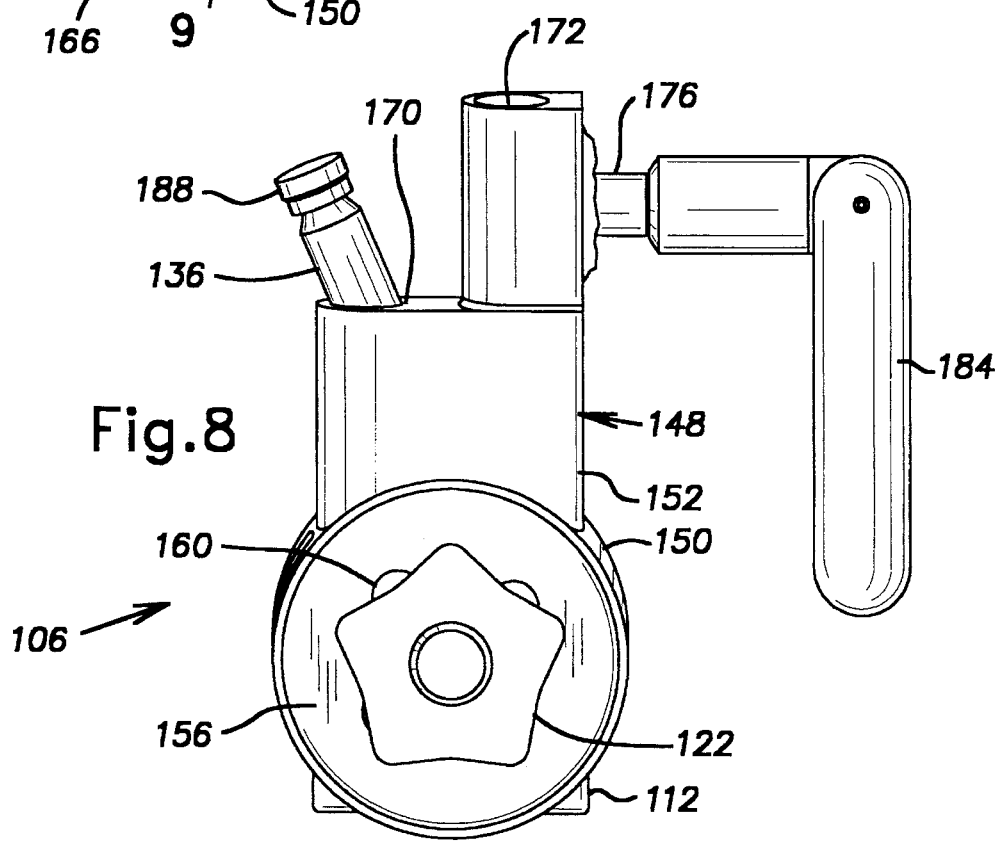
FIG. 8 is a front elevational view of the ratcheting table clamp of FIG. 7.
Figure 9:
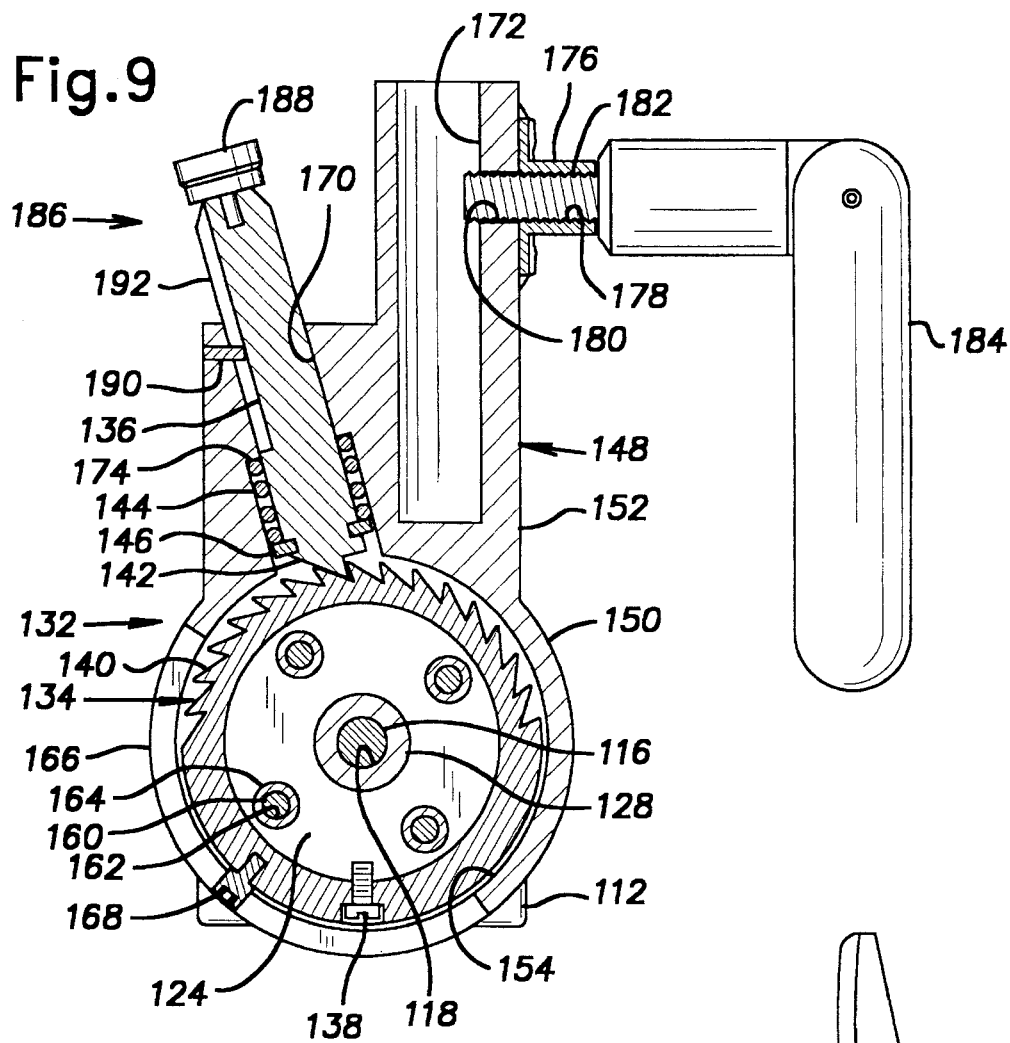
FIG. 9 is a cross-sectional view taken along line 9—9 of FIG. 7.

The ratcheting table clamp 106 is shown in FIGS. 7, 8, and 9. As best seen in FIG. 7, the table clamp 106 includes an attachment 112 which has a clamping portion 114 that is generally C-shaped in cross-section and is sized and shaped to receive the side rail 108 of the table 110 (FIG. 10). A threaded rod 116 extends through a threaded opening 118 (FIG. 9) in the closed side of the clamping portion 114. The rod 116 has a first end within the clamping portion 114 that has an increased diameter. The increased diameter provides a clamping surface 120 for contacting the side rail 108 of the table 110 and also prevents the first end of the rod 116 from passing through the threaded opening 118 in the clamping portion 114. A second end of the threaded rod is provided with a handle 122 such that the rod 116 can be rotated to move the clamping surface 120 toward and away from the open end of the clamping portion 114.

An alternative and preferred clamping portion 214 is shown in FIGS. 11 and 12. The clamping portion 214 is generally C-shaped in cross-section and is sized and shaped to receive the side rail 108 of the table 110 (FIG. 10). Opposed walls 216 downwardly extend from the bottom of the clamping portion 214 to form an open space 218. A shaft 220 extends through openings in the opposed walls 216. An eccentric cam 222 is attached to the shaft 220 within the open space 218 by fastener 224. Attached to an outer end of the shaft 220 is a handle 226. A pin 228 has a first end 230 extends through an opening 232 in the clamping portion 214. A second end 234 of the pin 228 has an enlarged diameter which contacts the cam 222. A helical coil spring 236 is located on the pin 228 within the open space 218 to bias the second end of the pin 228 towards the cam 222. When the large diameter of the cam 222 is vertical (FIG. 12), the pin 228 is in its uppermost position within the clamping portion 214. The pin 228 is sized to clamp the side rail 108 of the table 110 (FIG. 10) when in this position. The cam 222 is sized and shaped to retain the shaft 220 between the walls 216 and provide an adequate distance of axial travel for the pin 228. To unclamp the side rail 108 of the table 110 (FIG. 10), the handle 226 is rotated to rotate the shaft 220 and cam 222 until the small diameter of the cam 222 is in the vertical position (FIG. 11). As the cam 222 rotates, the spring 236 biases the pin 228 against the cam 222 so that the first end 230 of the pin 228 moves downward until it is no longer within the clamping portion 214. Preferably, a pair of pins 238 are provided at the top of the clamping portion 214 to provide an upper clamping surface for the side rail 108 of the table 110 (FIG. 10).

As best seen in FIGS. 7 and 9, the attachment 112 also includes a mounting portion 124 and a spacer portion 126 connecting the mounting portion 124 to the clamping portion 114. The mounting portion 124 is cylindrically-shaped and has an opening 128 in which the rod 116 passes through to the threaded opening 118 of the clamping portion 114. The spacer portion 126 is generally wedge-shaped and circular in cross-section. The diameter of the mounting portion 124 is smaller than the diameter of the spacer portion 126 forming an annularly-shaped seat 130. The spacer portion 126 is angled such that the mounting portion 124 is angled downwardly. The spacer portion 126 is preferably sized such that the axis of the mounting portion 124 is angled downwardly.

The axis is preferably angled in the range from about 10 degrees to about thirty degrees and more preferably the axis is angled about 20 degrees. It will be noted that the spacer portion 126 could be sized for other angles. This angle causes the rotational plane of the vertical adjustable support 102 to extend outwardly at an angle from the side of the table 110 to automatically abduct the limbs of the patient as described above in the description of the first embodiment.

As best seen in FIG. 9, a ratchet mechanism 132 is fixed to the attachment 112 and allows the support arm 104 to rotate to fixed angular positions. The ratchet mechanism 132 includes a ratchet wheel 134 and a lock pin 136. An inner diameter of the ratchet wheel 134 is sized to receive the mounting portion 124 of the attachment 112 such that the ratchet wheel 134 is adjacent or near the seat 130. A mounting screw 138 extends from the ratchet wheel 134 to the mounting portion 124 of the attachment 112 to prevent rotation of the ratchet wheel 134. The outer diameter of the ratchet wheel 134 has a plurality of serrations 140. Each serration 140 has an angled upper edge and an angled lower edge. The ratchet wheel 134 of the illustrated embodiment has sixteen serrations 134 to lock the support arm 104 in sixteen fixed angular positions. The serrations are located so that the support arm is rotatable over an arc of about 180 degrees that is from about horizontal to about horizontal. It will be noted that a greater or fewer number of fixed angular positions could be provided or a greater, smaller, or different arc could be provided. Additionally, a limit to the angular positions that reduces patient risk due to excess hip flexion could also be provided as described above in the description of the first embodiment.

The lock pin 136 is generally cylindrically-shaped and has a protruding end 142 shaped to engage the ratchet wheel serrations 140. The lock pin 136 is urged into the serration 140 by a spring element 144. The spring element 144 is preferably a helical coil compression spring having an inner diameter sized to surround the lock pin 136 and is held on the lock pin 136 by a retaining ring 146.

As seen in FIGS. 7–9, the table clamp 106 also includes a housing 148 which supports the support arm 104. The housing 148 has a generally cylindrically-shaped first portion 150 and generally rectangularly-shaped second portion 152 radially extending from the first portion 150. The first portion 150 has a cylindrically-shaped cavity 154 open at both ends with a diameter sized to receive the ratchet wheel 134. The housing 148 is retained about the ratchet wheel 134 by a cover plate 156 and a retaining ring 158. The cover plate 156 has an outer diameter generally equal to the diameter of the first portion 150 of the housing 148. The cover plate 156 is fixed to the mounting portion 124 of the attachment 112 by four mounting screws 160 extending into threaded openings 162 in the mounting portion 124 of the attachment 112. Spacers 164 are provided to space the cover plate 156 an adequate distance from the mounting portion 124 of the attachment 112. The retaining ring 158 is annularly-shaped having an outer diameter generally equal to the first portion 150 of the housing 148 and an inner diameter sized to receive the mounting portion 124 of the attachment 112. The retaining ring 158 is located between the seat 130 of the attachment 112 and the housing 148. Assembled in this manner the housing 148 is free to rotate about the ratchet wheel 134 on the axis of the mounting portion 124. Rotation of the housing 148 is limited by a stop such as slot 166 in the first portion 150 of the housing 148 and a screw 168 fixed to the ratchet wheel 134 as best seen in FIG. 9. The housing 148 is rotatable until the screw 168 contacts an end of the slot 166. The slot 166 is sized and located so that the housing 148 is rotatable only over an arc where the lock pin 136 engages the serrations 140 of the ratchet wheel 134.

The second portion 152 of the housing 148 has first and second bores 170, 172 perpendicular to the cavity 154 of the first portion 150. The first bore 170 is open at both ends and opens into the cavity 154. The first bore 170 has a step 174 between two diameters. A first diameter is adjacent the cavity 154 and is sized for receiving the spring element 144 and a second diameter is sized for receiving the lock pin 136. The second bore 172 is a blind bore and is sized to receive an end of the support arm 104. A support 176 having a threaded opening 178 is fixed, such as by welding, to the housing 148 adjacent an opening 180 which opens into the second bore 172. A threaded rod 182 extends cooperates with the threaded opening 178 of the support to clamp the support arm 104 within the second bore 172. A handle 184 is provided at an outer end of the rod 182 such that the rod 182 can be turned to move the rod 182 into and out of the second bore 172.

A ratchet release 186 is provided which disengages the lock pin 136 from the serration 140 and allows the support arm 104 to rotate back to the fixed angular positions. The ratchet release 186 includes a knob 188 located at an outer end of the lock pin 136. When the knob 188 is pulled outwardly with a force adequate to overcome the spring element 144, the spring element 144 is compressed against the step 174 and the protruding end 142 of the lock pin 136 disengages from the serration 140 of the ratchet wheel 134. Outward movement of the lock pin 136 is limited by a pin 190 fixed to the housing 148 which engages an end of an axially extending groove 192 on the lock pin 136.

Referring to FIG. 10, the invention is shown in a leg support application. The ratcheting table clamp 106 is removably secured to the side rail 108 of the operating room table 110 and the support arm 104 is received by table clamp 106. Due to the angle of the table clamp 106, the support arm 104 extends angularly outwardly in a lateral direction from the side of the table 110. The adjustable support 12 is received on the support arm 104 of the vertically adjustable support 102. The adjustable support 12 receives the connecting rod 11 of the boot 10. A second system according to the invention is typically secured to the opposed side of the table (not shown). The second system is a mirror image of the first such that the support arm extends outwardly in a lateral direction from the opposed side of the table. In this configuration a patient lies with their back on the table and a leg portion or foot in each boot 10.

The orientation and position of the leg can be adjusted by both the adjustable support 12 and the vertically adjustable support 102 as described above for the first embodiment. To disengage the ratchet mechanism, however, the knob 188 (FIG. 10) is pulled instead of turning the handle 70 (FIG. 5).

Although particular embodiments of the adjustable limb support system have been illustrated and described in detail, it will be understood that the invention is not limited correspondingly in scope, but includes all changes and modifications coming within the spirit and terms of the claims appended hereto.

What is claimed is:

1. An adjustable limb support system for an operating room table, said support system comprising:

a limb support;

an adjustable support for orienting said limb support; and a vertically adjustable support for positioning said limb support and said adjustable support in at least two fixed positions, said vertically adjustable support comprising a support arm secured to said adjustable support and a ratcheting table clamp, said ratcheting table clamp including a ratchet wheel having a central axis at an angle relative to horizontal, a housing rotatable about said central axis of said ratchet wheel and having first and second bores perpendicular to the central axis of the ratchet wheel, a lock pin carried within said first bore of said housing and engaging said ratchet wheel to allow only upward rotation of said housing to said fixed positions, a ratchet release for disengaging said lock pin from said ratchet wheel to allow downward rotation of said housing to said fixed positions, means for removably securing said support arm within in said second bore, and an attachment fixed to said ratchet wheel for securing said vertical adjustable support to the operating room table.

2. The adjustable support system according to claim 1, wherein said second bore of said housing is a blind bore.

3. The adjustable limb support system according to claim 1, wherein said axis rotation is at an angle of about twenty degrees from horizontal.

4. The adjustable limb support system according to claim 1, wherein said attachment has a clamping portion generally C-shaped in cross-section with closed and open sides, said closed side of said clamping portion having a threaded opening, and said attachment has a threaded rod cooperating with said threaded opening such that rotation of said rod moves an end of said rod toward and away from said open side of said clamping portion.

5. The adjustable support system according to claim 4, wherein said rod has a handle for rotating said rod.

6. The adjustable support system according to claim 4, wherein said attachment has a mounting portion angularly extending from said clamping portion, said ratcheting mechanism being fixed to said mounting portion.

7. The adjustable limb support system according to claim 1, wherein said means for removably securing said support arm in said second bore includes a threaded opening in said housing at said second bore and a threaded rod cooperating with said threaded opening such that rotation of said rod moves an end of said rod into and out of said second bore for removably clamping said support arm in said second bore.

8. The adjustable support system according to claim 7, wherein said rod has a handle for rotating said rod.

9. The adjustable support system according to claim 1, wherein said ratchet release comprises a knob fixed to said lock pin for outwardly pulling said lock pin to disengage said lock pin from said ratchet wheel.

10. The adjustable support system according to claim 1, wherein said central axis of said ratchet wheel is at an angle to horizontal in the range of about 10 degrees to about 30 degrees.

11. The adjustable support system according to claim 1, wherein said housing has a stop for limiting rotation of said housing and said support arm about said ratchet wheel.

12. The adjustable support according to claim 11, wherein said support arm rotates upwardly from about horizontal for about 180 degrees.

13. The adjustable support system according to claim 11, wherein said support arm rotates to a maximum angle of about 78 degrees relative to said operating room table for reducing patient risk.

14. A ratcheting table clamp for securing an end of a support arm to an operating room table, said table clamp comprising:

a ratchet wheel having a central axis at an angle relative to horizontal and a periphery with a plurality of serrations;

a housing rotatable about said central axis of said ratchet wheel having first and second bores generally perpendicular to the central axis of the ratchet wheel, said second bore sized for receiving the end of the support arm;

a lock pin carried by said housing within said first bore and having a protruding end adapted for engaging said ratchet wheel to allow rotation of said housing in only one direction;

a spring element for urging said protruding end of said lock pin into engagement with said serrations;

a knob secured to said lock pin for disengaging said lock pin from said ratchet wheel to allow rotation of said housing; and an attachment fixed to said ratchet wheel having a clamping portion for clamping to the operating room table.

15. The table clamp according to claim 14, wherein said second bore of said housing is a blind bore.

16. The table clamp according to claim 14, wherein said central axis of said ratchet wheel is at an angle to horizontal in the range of about 10 degrees to about 30 degrees.

17. The table clamp according to claim 14, wherein said central axis of said ratchet wheel is at an angle of about twenty degrees from horizontal.

18. The adjustable limb support system according to claim 14, wherein said clamping portion is generally C-shaped in cross-section with closed and open sides, and said attachment has a pin extending into said clamping portion perpendicular to said closed and open sides, a rotatable eccentric cam, and a spring for biasing said pin against said cam, said cam cooperating with said pin such that rotation of said cam moves an end of said pin within said clamping portion.

19. The adjustable limb support system according to claim 14, wherein said housing has a threaded opening at said bore, and a threaded rod cooperating with said threaded opening such that rotation of said rod moves an end of said rod into and out of said bore for removably clamping said support arm in said bore.

20. The adjustable support system according to claim 14, wherein said housing has a stop for limiting rotation of said housing about said ratchet wheel.

* * * * *